(12) United States Patent
Neu

(10) Patent No.: US 10,788,305 B1
(45) Date of Patent: Sep. 29, 2020

(54) DEVICE FOR RECORDING HEIGHT

(71) Applicant: Mark Neu, St Cloud, MN (US)

(72) Inventor: Mark Neu, St Cloud, MN (US)

(*) Notice: Subject to any disclaimer, the term of this patent is extended or adjusted under 35 U.S.C. 154(b) by 175 days.

(21) Appl. No.: 16/221,780

(22) Filed: Dec. 17, 2018

(51) Int. Cl.
*G01B 5/06* (2006.01)
*G01B 5/00* (2006.01)
*G01B 3/00* (2006.01)

(52) U.S. Cl.
CPC ............ *G01B 5/061* (2013.01); *G01B 5/0004* (2013.01); *G01B 3/004* (2013.01)

(58) Field of Classification Search
CPC .......... G01B 5/061; G01B 5/063; G01B 5/065
USPC ................................................... 33/511, 512
See application file for complete search history.

(56) References Cited

U.S. PATENT DOCUMENTS

| | | | | |
|---|---|---|---|---|
| 1,974,085 A * | 9/1934 | Shields | ............... | A61B 5/1072 33/512 |
| 2,215,884 A * | 9/1940 | Runge | .................. | A61B 5/1072 33/512 |
| 2,313,920 A * | 3/1943 | Campbell | .............. | G01F 23/42 33/484 |
| 2,369,988 A * | 2/1945 | Steckler | ............... | A61B 5/1072 434/187 |
| 2,381,428 A * | 8/1945 | Attick | .................. | A61B 5/1072 33/512 |
| 4,196,521 A * | 4/1980 | Hutchinson | ............. | G01B 3/08 33/494 |
| 5,402,585 A * | 4/1995 | Lund | ...................... | A61B 5/107 33/484 |
| 6,226,881 B1 * | 5/2001 | Landauer | ............... | G01B 5/061 33/511 |
| 6,599,045 B1 * | 7/2003 | Kolb | ...................... | B43K 29/00 33/18.2 |
| 7,155,838 B2 * | 1/2007 | Leyden | ................ | A61B 5/1072 33/492 |
| 7,181,861 B1 | 2/2007 | Leser | | |
| 7,770,301 B1 * | 8/2010 | Grandberry | .............. | G01B 3/04 33/494 |
| 9,658,058 B1 | 5/2017 | Jones | | |
| 2004/0111909 A1 * | 6/2004 | Pourmanafzadeh | ........ | A61B 5/1072 33/512 |
| 2012/0096726 A1 * | 4/2012 | Glock, Jr. | ............ | A61B 5/1072 33/512 |
| 2012/0144686 A1 * | 6/2012 | Haykeen | .............. | A61B 5/1072 33/512 |
| 2012/0285269 A1 * | 11/2012 | Cozen | .................... | G01B 5/061 73/865.4 |
| 2013/0091718 A1 * | 4/2013 | Haykeen | .............. | A61B 5/1072 33/512 |

(Continued)

*Primary Examiner* — George B Bennett
(74) *Attorney, Agent, or Firm* — Sanchelima & Associates, P.A.; Christian Sanchelima; Jesus Sanchelima

(57) ABSTRACT

A device for measuring and/or marking height is disclosed. The device comprises a rear section, side sections coupled to the rear section. Further, the device comprises a front section coupled to the side sections. The side sections comprise a rod receiving section. Further, the device comprises a rod coupled to the rod receiving sections. The device comprises a paper wound onto the rod, in which one end is coupled to the rod. The device is coupled to a wall or a door at a height from the ground and free end of paper is pulled down to mark height of a user and the paper is made to retrieve into the device when not in use.

5 Claims, 4 Drawing Sheets

(56) References Cited

U.S. PATENT DOCUMENTS

| | | | |
|---|---|---|---|
| 2014/0202017 A1* | 7/2014 | Wood | G01B 3/20 |
| | | | 33/512 |
| 2015/0219432 A1 | 8/2015 | Liu | |
| 2017/0254631 A1* | 9/2017 | Lee | A61B 5/1072 |
| 2018/0023945 A1* | 1/2018 | Mariller | G01B 5/14 |
| | | | 33/832 |

* cited by examiner

DEVICE FOR RECORDING HEIGHT

BACKGROUND OF THE INVENTION

1. Field of the Invention

The present disclosure generally relates to a height measuring/marking instrument. More particularly, the present disclosure relates to a device used for recording height of a user and that portable and detachably coupled to a wall or door.

2. Description of the Related Art

It is common that people generally wish to measure their height and weight from time to time. For instance, parents and/or children are to eager to know height of the child and their growth rate.

Conventionally, people measure height using variety of devices or instruments. Some of the devices or instruments include measuring tape, wall mounted scale, and so on. With increase in use of technology, people started to use electronic measurement devices that capture the vertical position of a person electronically and report the corresponding height measurement, by physically placing a device on top of a person's head, calculating the person's height by measuring the distance from the floor to the ceiling, and then subtracting the distance from the person's head to the ceiling.

As such, several types of height measuring devices have been disclosed in the past. One such height measuring device is disclosed in a U.S. Pat. No. 7,181,861. In U.S. Pat. No. 7,181,861, a device to measure the height of a person consisting of an elongated base that extends from above the head of the person being measured to the flat surface on which the person stands and a sliding member is disclosed. The base has two longitudinal channels, one containing a T-track and the other a measuring scale. There is a blank surface on which to record the height and other additional data. Decorative indicia may also be placed on the blank area. The vertically movable sliding member has a forward extending bar that rests against the top of the head of the person being measured. A follower extends from the side of the sliding member across the channel containing the scale. The top edge of the follower is at the same level as the bottom surface of the bar. The height can be read along the top edge of the follower.

Another example is disclosed in a United States patent application 20150219432. In US20150219432A1, a height measurement device, detachably disposed on an article, including a body and a measurement unit is disclosed. The body includes a clamping member, a stopper and a pivot member. The clamping member has a first joint portion and a clamping slit, wherein the clamping slit is capable of clamping the article. The stopper has a first pivot portion. The pivot member has an adjacent portion and a second joint portion, and is pivotally jointed the stopper to the clamping member through the first pivot portion, whereas the pivot member is moved to allow the second joint portion joint to the first joint portion, the adjacent portion abuts the stopper onto the clamping member so as to fix the stopper at a measurement position. The measurement unit disposed on the body is for use in measuring a height of the measurement position.

Another example is disclosed in a United States patent application 20170254631. In US20170254631A1, it is disclosed that a height measuring device is movably positioned on a scale surface, the height measuring device comprises: a bracket repeatedly attached to or detached from the scale surface; and a measuring unit assembled with the bracket, wherein the measuring unit includes a folding position and an extending position relative to the bracket, the measuring unit is close to the bracket in the folding position, and the measuring unit is perpendicular to the scale surface in the extending position.

Another example is disclosed in a U.S. Pat. No. 9,658,058. In U.S. Pat. No. 9,658,058B1, an apparatus, system and method for measuring height of one or more objects/users is disclosed. Once the height measuring device is calibrated, a retracting foot platform is positioned atop a user/object and its distance is captured, stored and calculated by a distance sensor to determine the resulting heights of the objects/users. The distance sensors may come in the form of a linear encoder or a rotary encoder. The height measurements may be displayed on a screen, including the screen display of the height measuring device itself, or other devices such as a tablet, smartphone or scale. The height data from each user/object may be compared to one another. The height measuring device also includes a predictive algorithm that determines the future height of one or more users.

Although the above height measuring devices are capable of measuring height accurately, they have several disadvantages. For instance, the devices discussed above are bulky. Further, they are securely affixed to wall. As a result, it is very difficult to carry or move them from one place to another. Further, when the height measuring devices which utilizes a scale to measure height of the user, users tend to write or mark on the walls. This can be destructive to the walls and/or lost over time. Furthermore, the height measuring devices discussed above are relatively expensive and heavy and must either be stored when not in use or allowed to occupy valuable living space.

Other documents describing the closest subject matter provide for a number of more or less complicated features that fail to solve the problem in an efficient and economical way. None of these patents suggest the novel features of the present invention. Specifically, none of the disclosures in the art disclose a device that can be detachably coupled to a wall or door and can be used to measure and/or record height and keep the data for a long time.

Therefore, there is a need in the art for a device that can be detachably coupled to a wall or door and can be used to measure and/or mark height and keep the data for a long time.

SUMMARY OF THE INVENTION

It is one of the main objects of the present invention to provide a device that can be used to measure and/or mark height and that avoids the drawbacks of the prior art.

It is one object of the present invention to provide a device comprising a paper that can be used to record height of a user and retrieve upon use.

It is another object of the present invention to provide a device that can be detachably coupled to a wall or door.

It is one object of the present invention to provide a device for measuring and/or marking height. The device comprises a rear section, side sections coupled to the rear section. Further, the device comprises a front section coupled to the side sections. The side sections comprise a rod receiving section. Further, the device comprises a rod coupled to the rod receiving sections. The device comprises a paper wound onto the rod, in which one end is coupled to the rod. The device is coupled to a wall or a door at a height from the ground and free end of paper is pulled down to mark height of a user and the paper is made to retrieve into the device when not in use.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

The following detailed description is intended to provide example implementations to one of ordinary skill in the art, and is not intended to limit the invention to the explicit disclosure, as one or ordinary skill in the art will understand that variations can be substituted that are within the scope of the invention as described.

The present disclosure discloses a device for measuring and/or marking height. The device comprises a rear section, side sections coupled to the rear section. Further, the device comprises a front section coupled to the side sections. The side sections comprise a rod receiving section. Further, the device comprises a rod coupled to the rod receiving sections. The device comprises a paper wound onto the rod, in which one end is coupled to the rod. The device is coupled to a wall or a door at a height from the ground and free end of paper is pulled down to mark height of a user and the paper is made to retrieve into the device when not in use.

Various features and embodiments of a device are explained in conjunction with the description of FIGS. 1-6.

Figure 1:
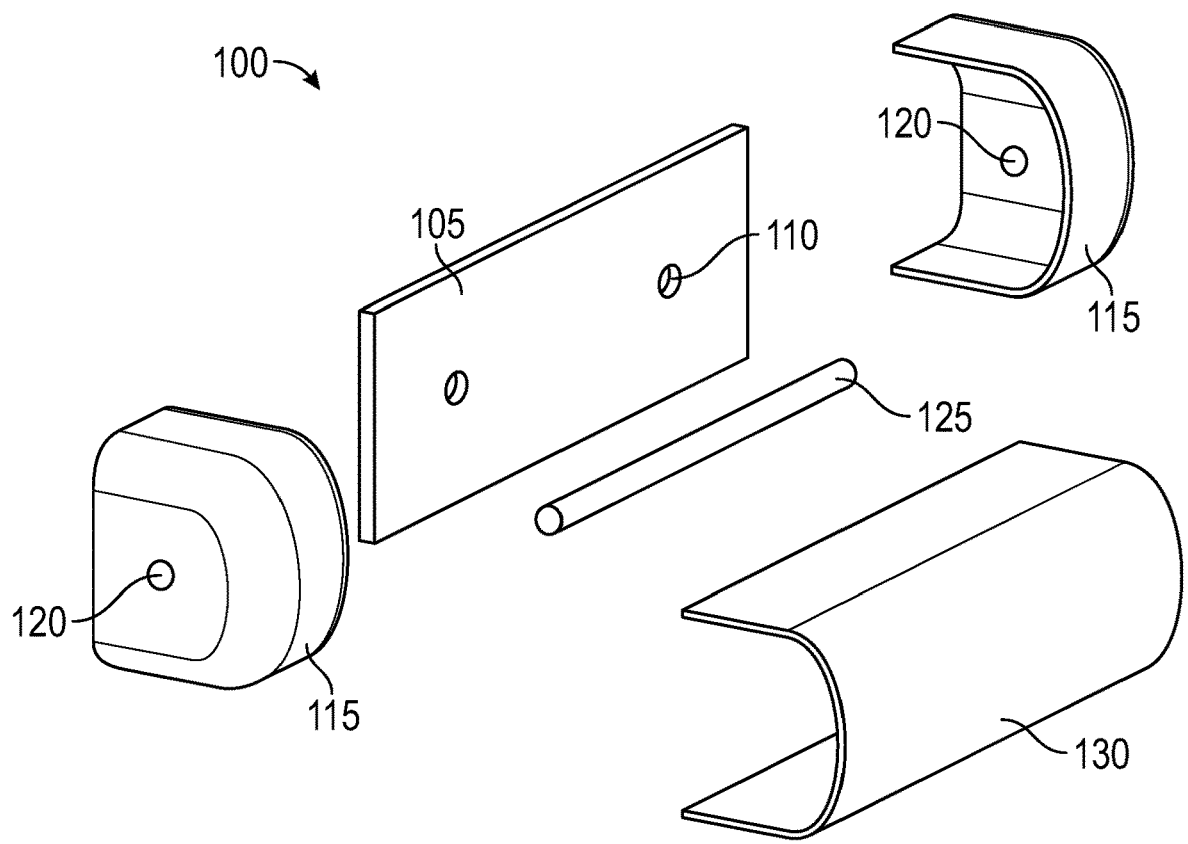
FIG. 1 illustrates an exploded view of a device 100, in accordance with one embodiment of the present disclosure.

Referring to FIG. 1, an exploded view of a device 100 for measuring and/or recording height of people is shown, in accordance with one embodiment of the present disclosure. The device 100 comprises a rear section 105. The rear section 105 may be provided with holes 110. The device 100 comprises side sections 115. Each of the side sections 115 comprises a rod receiving section 120. The rod receiving sections 120 are used to receive a rod 125. In one implementation, the rod 125 comprises a spring member (not shown).

It should be understood that the side sections 115 might be provided in a semicircular to circular shape. It is to be noted that the side sections 115 may be made up of plastic, metal or any other suitable material.

Further, the device 100 comprises a front section 130. The front section 130 is provided in a cylindrical shape. In other words, the front section 130 is provided in a semi-circular shape. Although the front section 130 is shown in cylindrical or semi-circular, it is obvious to a person skilled in the art to provide the front section 130 in rectangular shape.

It should be understood that each of the rear section 105, the side sections 115, the front section 130 may be made up of one of metal, plastic, wood and the like. Further, the rod 145 may be made using suitable materials such as metal, plastic, wood and the like.

Figure 2:
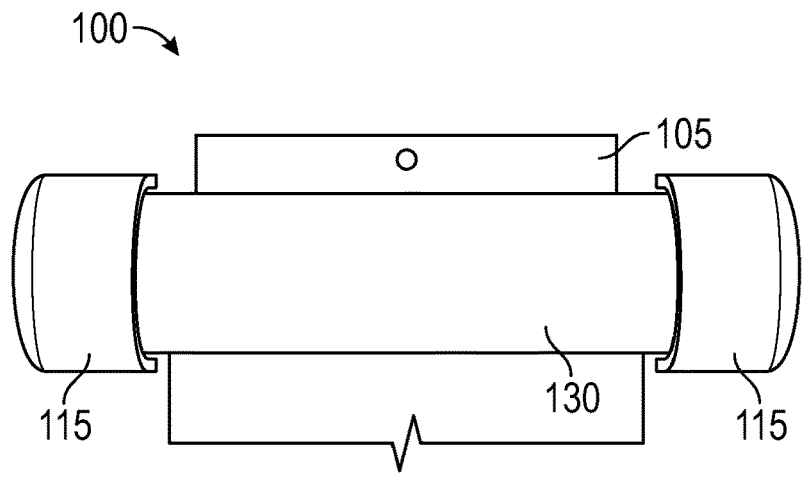
FIG. 2 illustrates the device 100, in accordance with one embodiment of the present disclosure.

Referring to FIG. 2, the device 100 is shown. As can be seen, the side sections 115 are coupled to the rear section 105. Further, the rod 125 is coupled to the side sections 115. Further the front section 115 is coupled to the side sections 115. It should be understood that rear section 105, the side sections 115, and the front section 130 are coupled using known mechanisms such as welding, adhesive, fasteners and so on.

Figures 3, 4:
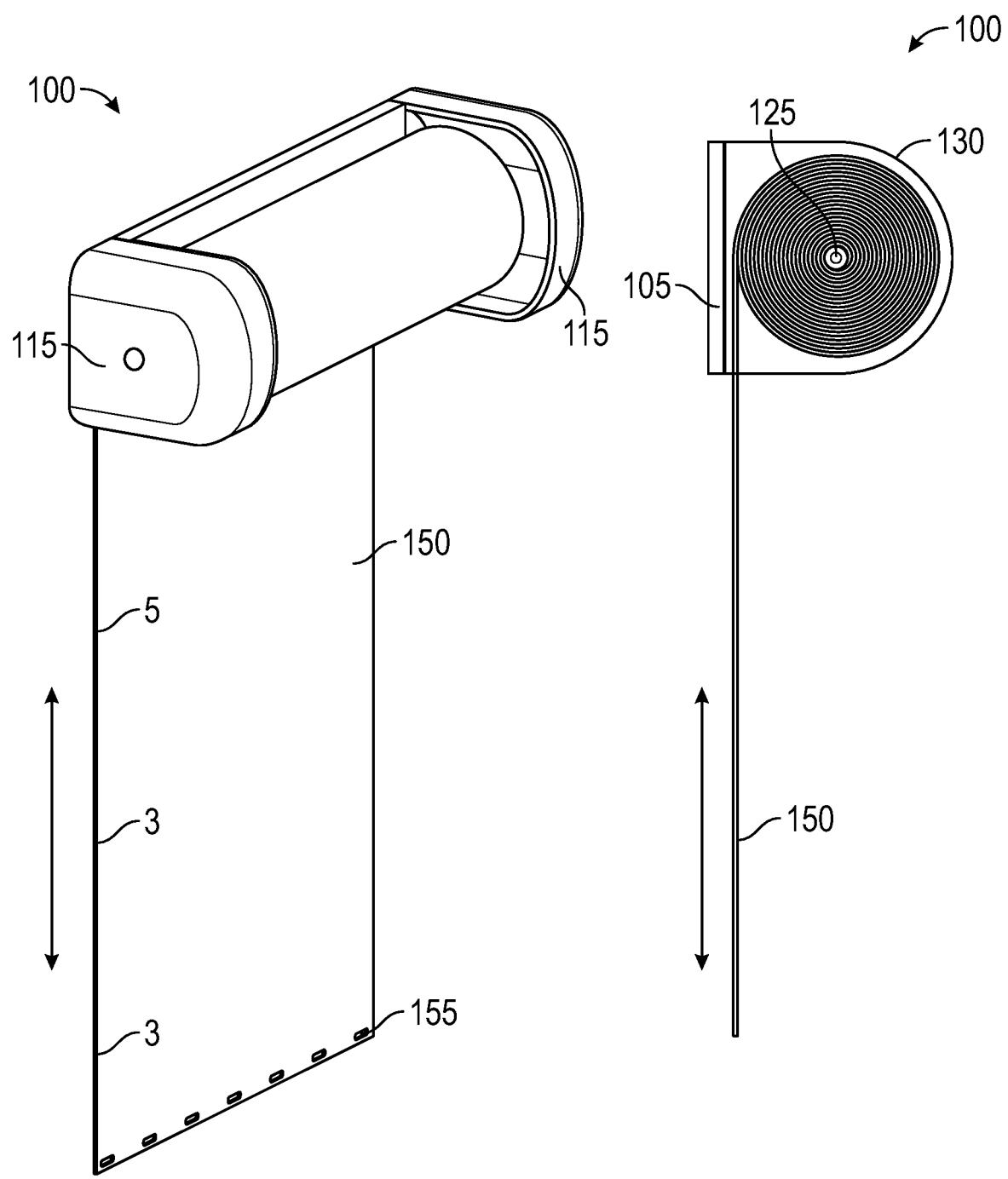
FIGS. 3 and 4 illustrate a perspective and side view of the device 100 respectively, in which the device 100 comprises a paper 150, in accordance with one embodiment of the present disclosure.

In one embodiment, the device 100 comprises a paper coupled to the rod 125. Referring to FIG. 3, a perspective view of the device 100 comprising a paper 150 is shown, in accordance with one embodiment of the present disclosure. Further, referring to FIG. 4, a side view of the device 100 comprising the paper 150 is shown. The paper 150 may include a bendable paper that is made of synthetic resin like polyvinyl and made of a material that is able to receive marks such as letters, symbols and the like thereto by a pen, pencil and the like.

It should be understood that one end of the paper 150 is coupled to the rod 125. Further, the paper 150 is rolled around the rod 125. Other end i.e., free end of the paper 150 is drawn through a gap provided between the front section 130 and the rear section 105 as shown in FIG. 4. Further, the paper 150 may be provided with a plurality of grooves 155 at open end of the paper 150 as shown in FIG. 3.

Figure 5:
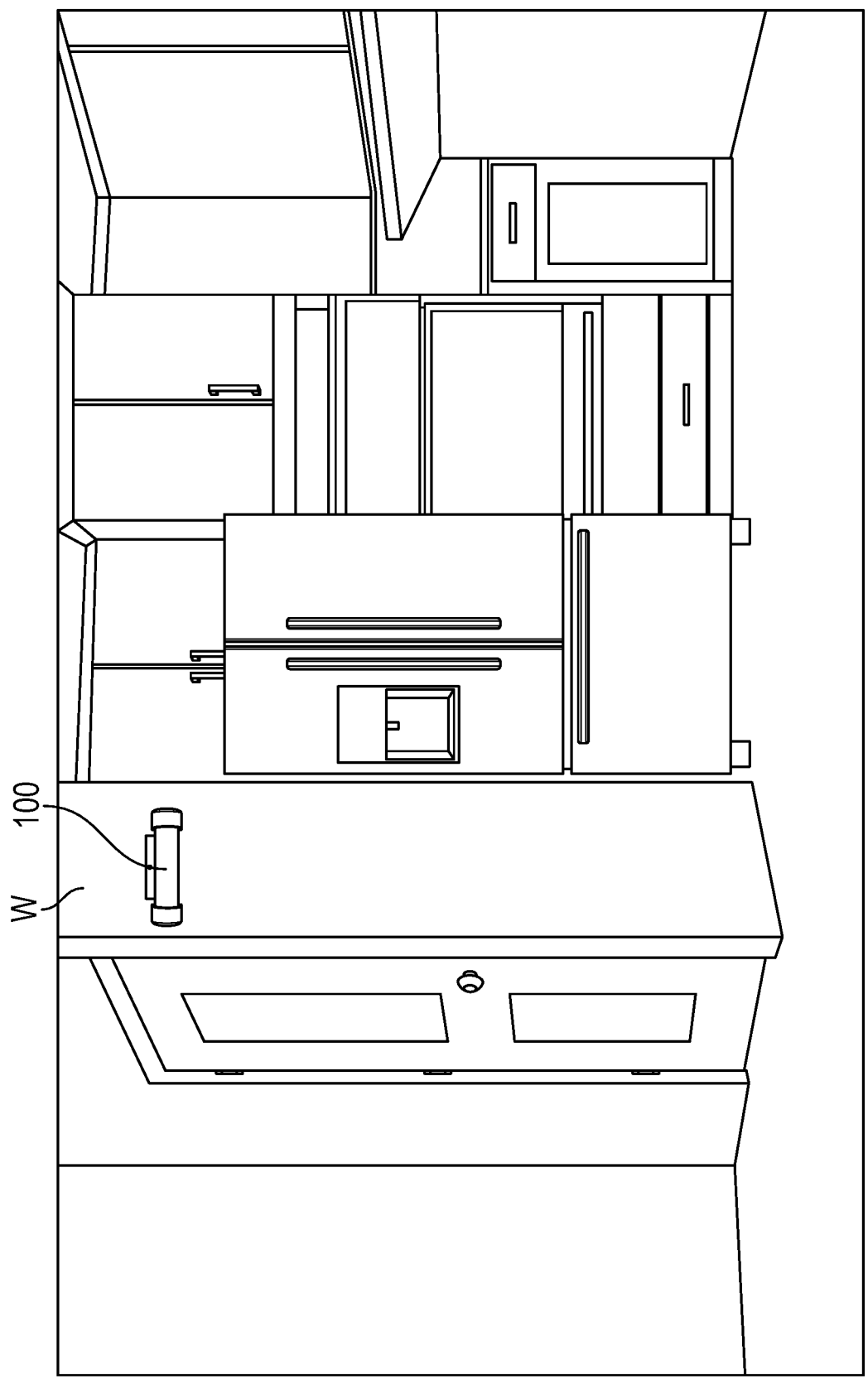
FIG. 5 illustrates the device 100 coupled to a wall W, in accordance with one embodiment of the present disclosure.

Referring to FIG. 5, the device 100 coupled to a wall W is shown, in accordance with one exemplary embodiment of the present disclosure. The device 100 may be used for measuring and/or recording height of occupants of a house. As discussed above, parents and children are eager to know height of the child and their growth rate. As can be seen from FIG. 5, the device 100 may be coupled to the wall W at certain height. For example, the device 100 may be coupled to the wall W at a height of seven feet from the ground. In another example, the device 100 may be coupled to the wall W at a height of at least five feet from the ground. Although it is shown that the device 100 is coupled to the wall W, it is obvious to a person skilled in the art to couple the device 100 to a door or refrigerator or any other standing structure in the house.

In order to couple the device 100 to the wall W or to the door, at first, the rear section 105 is coupled to the wall W. Specifically, the rear section 105 is coupled to the wall W with the help of the holes 110 provided in the rear section 105. In one example, fasteners may be used to secure the rear section 105 of the device 100 to the wall W. In one example, the rear section 105 of the device 100 may be secured to the wall W using other known mechanism such as adhesives, Velcro and so on.

Figure 6:
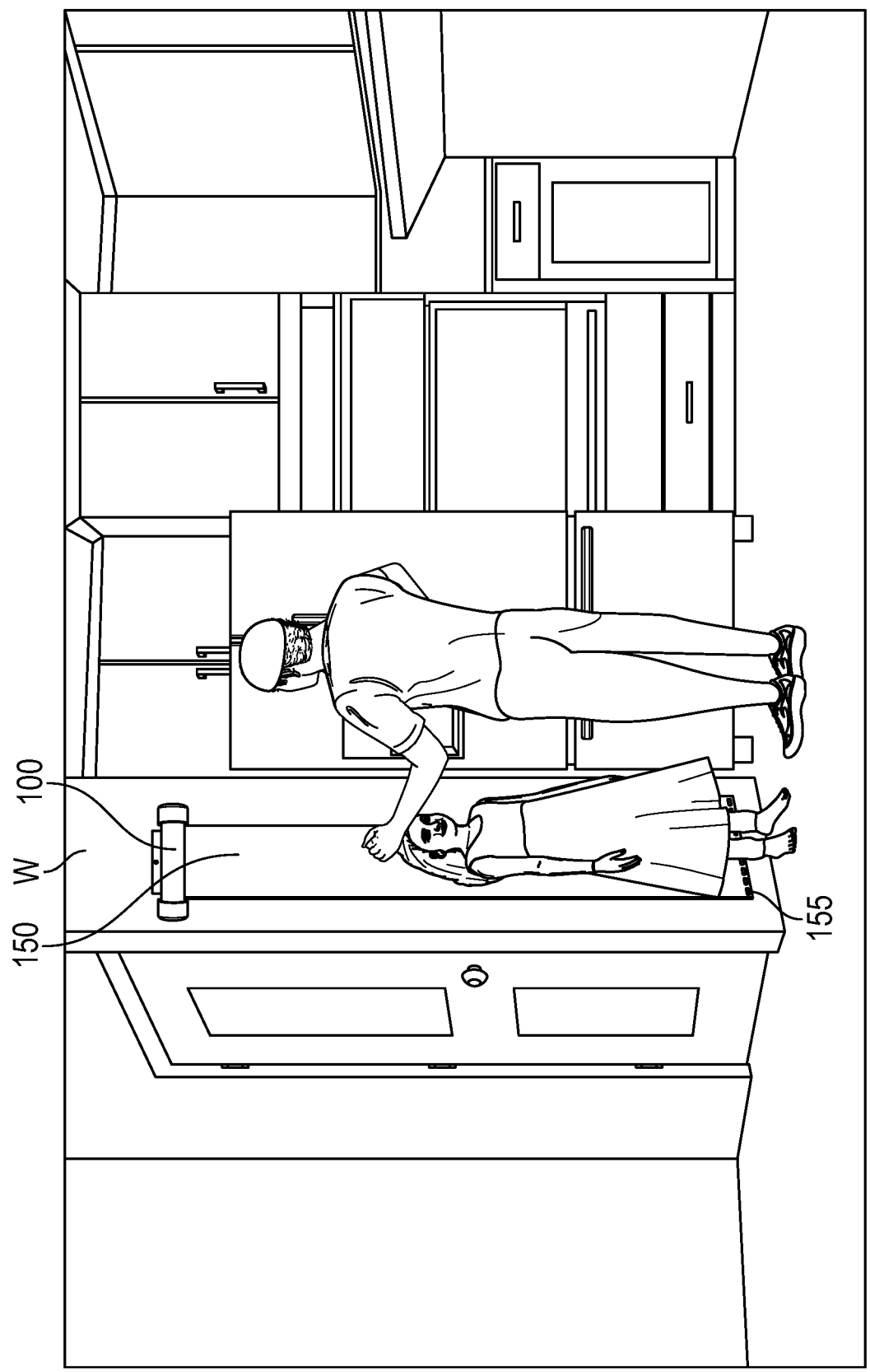
FIG. 6 illustrates the device 100 used for measuring or marking height of a user, in accordance with one embodiment of the present disclosure.

Whenever a user wishes to measure and/or record height, the user may hold the free end of the paper 150 and pull down the paper 150 towards the ground. After pulling down the paper 150, the user may secure the paper 150 to the wall W with the help of the plurality of grooves 155 at the end of the paper 150 thereby ensuring that the paper 150 is opened and locked/secured, as shown in FIG. 6. After locking the paper 150 to the wall W, the user may ask the child to stand near the paper 150 or he himself may stand near the paper 150 and leave a mark on the paper 150 corresponding to the height. In one example, the user may leave a mark and write name and age of the child. Further, the user may mark date in which the height is marked on the paper 150. It should be obvious to a person skilled in the art to leave a mark of user's choice to indicate date, name, symbols, characters, and height of the user or the child among other data on the paper 150. After marking the height of the child on the paper 150, the user may decouple the paper 150 i.e., plurality of grooves 155 at the end of the paper 150 such that the paper 150 is retracted into the device 100 i.e., into its original position shown in FIG. 5.

It is to be understood that the paper 150 is made to retract due to the presence of the spring member in the rod 145. In other words, whenever the open end of the paper 150 is not secured to the wall W, then the spring member exerts pressure to wound the paper 150 such that the paper 150 is rolled around the rod 145. Further, whenever the user wishes to record or mark height of the user or child, then the user may hold the open end of the paper 150 and secure the paper 150 to the wall W as shown in FIG. 6. After securing, the user may record or mark the height. After marking height, the paper 150 is decoupled from the wall W and made to retract to its original position, as shown in FIG. 5.

In one implementation, the user may operate the rod 145 in circular motion or rotate the rod 145 to wound or retract the paper 150 onto the rod 125.

In one implementation, the paper 150 may be printed with a scale such that the device 100 is affixed at a pre-defined height from the ground. Whenever, the user wishes to measure height, the user may pull down the paper 150 and secure the paper 150 to the wall W as explained above. After pulling down, the user may stand near the paper 150 and measure his height corresponding to the scale and leave a mark on the paper 150 indicating his height on a particular date. After marking, the user may rotate the side sections to roll back the paper 150 onto the rod 125. In another example, after use, when the paper 150 is decoupled from the wall W, due to the presence of the spring member at the rod 125, the paper 150 may be rolled onto the rod 125 automatically.

Based on the above, it is evident that paper 150 may be used to measure or mark height of the user or child, and when not in use, the paper 150 is wound onto the rod 125 within the device 100.

In addition, data corresponding to height, age, date can be recorded or marked continuously on the paper easily and constantly, so that it can keep the data through the years of growth from the date of birth in efficiency, and the user can keep a history of an individual. In addition, the paper with marking indicating the height may be kept as memorial goods for life.

Further, the paper is wound within the device when not in use. As a result, the paper is not exposed to atmosphere when not in use and life of the paper is extended.

Further, the device can be easily coupled and removed from the wall or door due to its simplistic structure. As such, whenever the user is shifting house, the user can remove the device from old house and affix the device in the new house thereby retaining the memories of the child for a lifetime.

It should be understood that the paper might be provided in variety of shapes and designs. Further, the paper may be provided at varied length so that the paper may be used for prolonged time and/or to record height of various occupants in the house.

As presented above, the device may be coupled to the wall or to the door in the house; for example, the device may be coupled to the door of the children.

It should be understood that the terms marking and recording used herein indicate an impression that the user makes on the paper to determine height, name, age, date and so on.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for recording height of a user, comprising:
a rear section;
side sections coupled to the rear section;
a front section coupled to the side sections;
a rod receiving section provided at the side sections;
a rod coupled to the rod receiving sections; and
a paper wound onto the rod,
wherein the device is coupled to a wall or a door at a height from the ground, wherein the paper is pulled down to mark height of a user and the paper is retrieved into the device.

2. The device of claim 1, wherein the open end of the paper is drawn through the front section.

3. The device of claim 1, wherein the rod comprises a spring member used to retract the paper when not in use.

4. The device of claim 1, wherein the paper comprises a plurality of grooves at the free end, used for coupling the paper to the wall or the door.

5. The device of claim 1, wherein the rear section comprises holes used to couple the device to the wall or the door.

* * * * *